United States Patent [19]

Foxman

[11] Patent Number: 4,939,017

[45] Date of Patent: * Jul. 3, 1990

[54] ABSORPTIVE DEVICE WITH PROTECTIVE POCKETS

[75] Inventor: Charles Foxman, St. Louis County, Mo.

[73] Assignee: Medpat, Inc., Maryland Heights, Mo.

[ * ] Notice: The portion of the term of this patent subsequent to Jul. 4, 2006 has been disclaimed.

[21] Appl. No.: 189,151

[22] Filed: May 22, 1988

Related U.S. Application Data

[63] Continuation-in-part of Ser. No. 148,023, Jan. 25, 1988, Pat. No. 4,844,965.

[51] Int. Cl.$^5$ .............................................. B32B 1/04
[52] U.S. Cl. ..................................... 428/192; 5/484; 428/121; 428/224; 428/296; 428/913; 604/380
[58] Field of Search ................... 5/484; 428/192, 284, 428/296, 913, 121; 604/380

[56] References Cited

U.S. PATENT DOCUMENTS

| 4,388,075 | 6/1983 | Mesek et al. | 428/913 |
| 4,610,352 | 9/1986 | Howey et al. | 428/296 |
| 4,655,877 | 4/1987 | Horimoto et al. | 428/296 |
| 4,659,614 | 4/1987 | Vitale | 428/296 |

Primary Examiner—James J. Bell
Attorney, Agent, or Firm—Polster, Polster and Lucchesi

[57] ABSTRACT

An absorptive device is disclosed as including a liquid permeable absorptive member which overlies a liquid impervious barrier member. The liquid permeable absorptive member has an outer facing layer of synthetic thermal plastic fabric and an inner backing layer with a material blend of thermal plastic and cellulosic fibers. The synthetic thermal plastic outer facing layer is ultrasonically welded to the thermal plastic fibers of the blended material inner backing layer to join the layers together while allowing liquid communication throughout the layers. The absorptive device further includes protective pockets/handles for lifting, folding and removing the absorptive device from a surface without exposure to the contents thereof.

10 Claims, 1 Drawing Sheet

ABSORPTIVE DEVICE WITH PROTECTIVE POCKETS

BACKGROUND OF THE INVENTION

This is a continuation-in-part of Ser. No. 148,023, filed Jan. 25, 1988 entitled ABSORPTIVE DEVICE FOR INCONTINENT PATIENTS, now U.S. Pat. No. 4,844,965.

This invention relates to absorptive devices with protective pockets/handles, and more particularly, to an incontinent pad absorptive device having protective pockets to lift, fold and remove an incontinent pad without exposure to the contents thereof.

As disclosed in my aforementioned parent patent application Ser. No. 148,023, filed Jan. 25, 1988, an absorptive device for incontinent patients includes a liquid permeable absorptive member and a liquid impervious barrier member. The liquid permeable absorptive member is composed of an outer facing layer of thermal plastic material and an inner facing layer made from a material blend of thermal plastic and cellulosic fibers. The thermal plastic material outer layer is ultrasonically welded to the thermal plastic fibers of the blended material inner backing layer to join the layers together while allowing liquid communication throughout the layers. The liquid impervious barrier member underlies the liquid permeable absorptive member to restrict the flow of liquid therethrough.

With an absorptive device constructed as described above, the synthetic material blend inner layer is quite absorptive, while permitting ultrasonic welding and thus durable fastening to the outer facing layer. The synthetic materials from which absorptive device is made are considerably lighter in weight then natural fabric products providing quicker drying time at lower temperatures. This results in obvious energy and time dollars saved during processing/cleaning of the absorptive device. The synthetic materials of the absorptive device also are wrinkle resistant, require little or no ironing, do not stick together when subjected to drier heat, are hypoallergenic, last considerably longer than natural fabric products, are odor and mildew resistant, are bacterial and fungal resistant, have soil release characteristics and meet government specifications for flame resistance.

In view of these and other advantages, the absorptive device which is disclosed and claimed in the aforementioned prior parent patent application has received broad customer acceptance and substantial commercial success in a wide variety of public and private institutions.

Where patients are not only incontinent, but also have highly contagious diseases, i.e., AIDS, the removal and disposal of incontinent pads, without causing exposure to the nurse or attendant, is an important consideration. Thus, even though the absorptive device functions effectively as an incontinent pad, unless some way is found to facilitate removal and/or disposal of such devices in cases where highly contagious disease are involved, the absorptive device may unnecessarily expose nurses or attendants to highly contagious diseases contained within the contents of the absorptive device.

SUMMARY OF THE INVENTION

Among the several objects and advantages of the present invention include:

An absorptive device which facilitates removal, following use, without exposure to the contents of the absorptive device;

An absorptive device of the type described which includes a liquid permeable absorptive member and a liquid impervious barrier member which facilitates removal of the absorptive device, following use, without contact with the liquid permeable absorptive member;

An absorptive device of the type described which enables lifting, folding and removal of the absorptive device from a surface without contact with the contents of the device;

An absorptive device of the type describe which includes all of the features and advantages of my prior aforementioned patent application, as well as those features and advantages set forth in this invention summary.

The foregoing and other objects and advantages are achieved by an absorptive device comprising a liquid permeable absorptive member having an outer facing layer material and an inner backing layer, the inner backing layer being a material blend of thermal plastic and cellulosic fibers. The outer facing layer is ultrasonically welded to the thermal plastic fibers of the inner backing layer to join the layer together, while allowing liquid communication throughout the layers. A liquid impervious barrier member underlies the liquid permeable absorptive member and restricts the flow of liquid therethrough. Protective pockets or handles are attached to the liquid impervious member for lifting, and folding the absorptive device without any contact with the contents thereof.

The above and other objects and advantages of the present invention will become apparent from the ensuing description.

BRIEF DESCRIPTION OF THE DRAWINGS

In the drawings.

Corresponding reference numerals are used throughout the various view of the drawings.

DESCRIPTION OF THE PREFERRED EMBODIMENT

Figure 1:
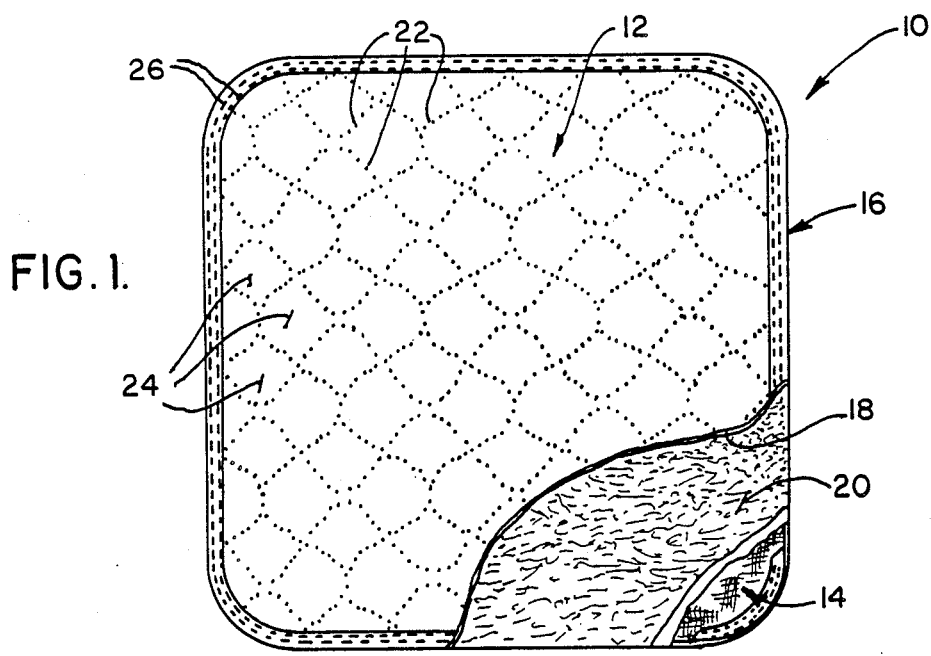
FIG. 1 is a top view of an absorptive device which is constructed in accordance with the teachings of the present invention, in which the lower right hand corner thereof had been exposed to reveal the various layers and/or membranes of the absorptive device.

The construction of the absorptive device 10 corresponds to the absorptive device disclosed in my aforementioned copending patent application. Specifically, the absorptive device 10 includes a liquid permeable absorptive member 12, a liquid impervious barrier member 14 and liquid impervious side binding member 16, the latter joining in holding the liquid permeable absorptive member 12 and liquid pervious barrier member 14 to one another.

The liquid permeable absorptive member 12 includes an outer facing layer of synthetic fabric 18 and an inner backing layer 20 having a material blend of thermal plastic and cellulosic fibers. The outer facing layer 18 is manufactured from a 100% synthetic thermal plastic fabric and provides a soft surface that breathes, enhancing patient comfort. The inner backing layer 20 of the liquid permeable absorptive member 12 is a blend of thermal plastic and cellulosic fibers which are aligned and punched with needles to gain material integrity. It has been discovered that this blend of material fibers is important in that it not only absorbs liquid quite readily, but permits the outer facing layer 18 to be ultrasonically welded to the thermal plastic fibers of the inner backing layer 20.

This ultrasonic welding of the layers 18, 20 is best seen in FIG. I of the drawings. For an even more detailed explanation, reference is made to my aforementioned copending patent application. In general, the thermal plastic fibers of the inner backing layer 20 are ultrasonically welded to closely spaced intersecting strands of the thermal plastic outer facing layer 18 at intermittent locations 22, and forming, preferably, a quilt pattern configuration 24 throughout the absorptive device 10. Each of the intermittent locations 22 is represented by a small circular welded area 22, and is to understood to constitute a bond between the synthetic thermal plastic fabric of the outer layer 18 and the thermal plastic fibers of the material blend in the inner backing layer 20. The result produces a simulated quilt pattern with a "threadless quilting" configuration in which the outer facing layer 18 and the inner backing layer 20 are fastened and supported by one another. At the same time, the intermittent locations between the ultrasonic welds 22 allows liquid communication throughout the layers 18, 20 in the absorptive device 10.

As shown in the drawings, the liquid impervious barrier member 14 comprises a single membrane or layer; however, in my prior aforementioned copending patent application, the liquid impervious barrier member 14 may comprise three layers or membranes for the purposes set forth. One of the chief features and advantages of the liquid impervious barrier member 14 is to prevent any liquid received and/or retained by the liquid permeable absorptive member 12 from passing through the liquid impervious barrier member 14.

Figure 2:
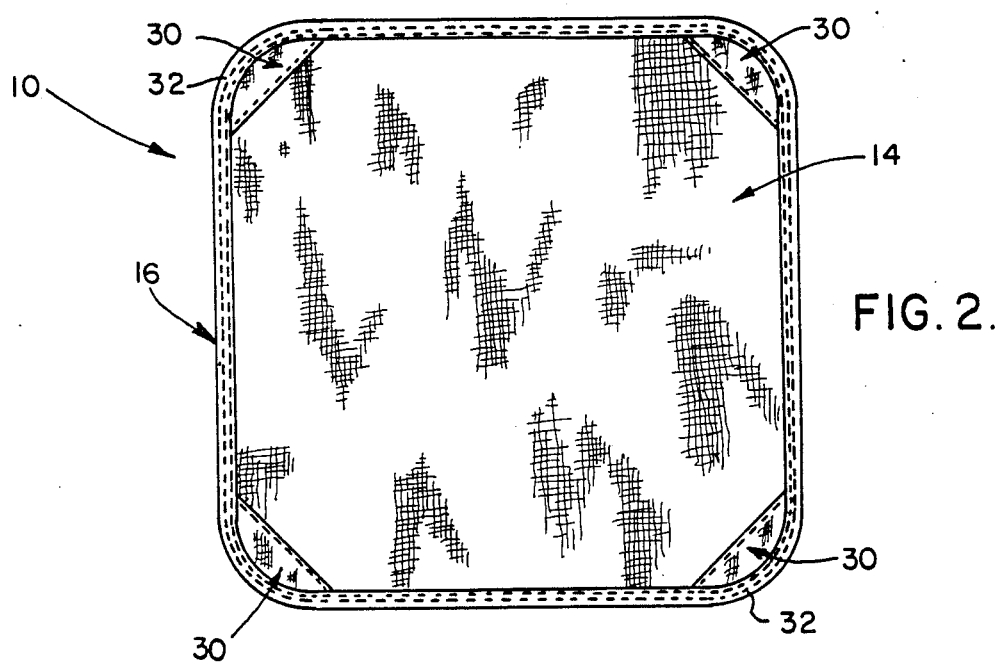
FIG. 2 is a bottom plan view of the absorptive device shown in FIG. 1, including protective pockets which extend diagonally across the rounded corner areas of the absorptive device.
Figure 3:
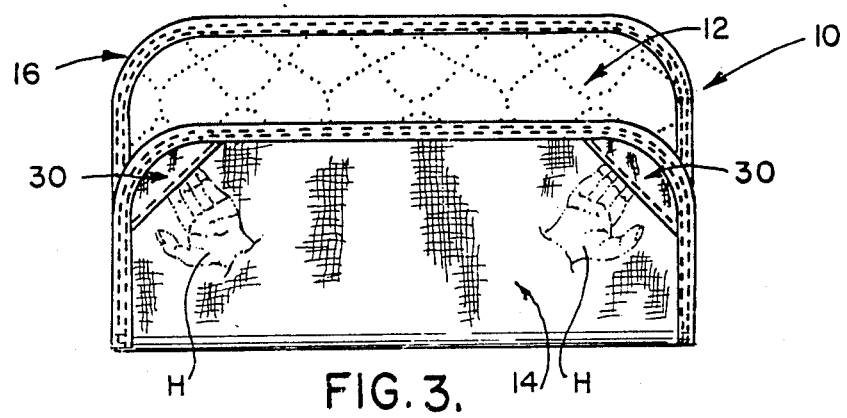
FIG. 3 is a combined partial bottom plan and top plan view of the absorptive device showing phantom hands engaging the protective pockets for lifting and removing the absorptive device from a surface, without exposure to the contents thereof.

In order to hold the liquid permeable absorptive member 12 and the liquid impervious barrier member 14 to one another along the outer free edges thereof, as well as to prevent side liquid leakage, the liquid impervious side binding member 16 is provided. The side binding members 16 comprises a generally U-shaped configuration which surrounds the outer free end surfaces of the liquid permeable absorptive member 12 and the liquid impervious barrier member 14, with a double needle lock stitch 26 being used to bind and secure for the U-shaped side binding members 16 to the liquid permeable absorptive member 12 and a liquid impervious barrier member 14, as shown in FIGS. 1-3 of the drawings. Preferably, the side binding member 16 is made from the same construction as the liquid impervious barrier member 14, in order that any liquid received within the liquid permeable absorptive member 12 will be retained within the confines thereof without passing through the liquid impervious barrier member 14 or the side binding member 16.

Absorptive devices 10 constructed in the aforementioned manner have received broad and universal commercial acceptance because of the many inherent features and advantages that have resulted, as set forth above. At the same time, it has been discovered that where the absorptive devices are used as incontinent pads and patients have highly contagious diseases i.e., AIDS, the removal and/or disposal of such devices, without causing exposure to nurses or attendants, has been difficult.

Accordingly, as an important feature of the present invention, the absorptive device lo includes sleeves or protective pockets 30 which are attached/associated relative to the liquid pervious barrier member 14 in order to enable lifting and folding of the absorptive device 10 without contacting the liquid permeable absorptive member 12. The protective pockets or handles 30 preferably extend diagonally across at least some of the rounded corner areas 32 of the generally square-shaped absorbent device 10 shown in the drawings The protective pockets 32 are also stitched and joined to the absorbent device 10 by being stitched to the side binding member 16 as shown in FIGS. 2-3 of the drawings. Thus, the protective pockets 32 extend in overhanging relationship to the liquid impervious barrier member 14, allowing lifting and removal of the absorbent device 10 from a surface, such as a bed. This is best illustrated in FIG. 3 of the drawings where the phantom hands H illustrate the manner in which the protective pockets 30 are engaged to lift, fold and remove the absorptive device 10 from a supporting surface, without contacting the liquid permeable absorptive member 12. Since the liquid impervious barrier member 14 and side binding member 16 allow no liquid to permeate therethrough, safe and effective removal of the absorptive device 10 from a supporting surface may be easily accomplished by engaging adjacent handle flaps 30, as illustrated in FIG. 3, for removing the absorptive device 10 without engaging any of the contents of the liquid permeable absorptive 12.

In view of the above, it will be seen that the present invention discloses an absorptive device with pockets which achieve the objects of the invention and produces many other advantageous results as well.

As various changes could be made in the above construction without departing from the scope of the invention, it is intended that all matter contained in the above description or shown in the accompanying drawings shall be interpreted as illustrative and not in a limiting sense.

I claim:

1. An absorptive device comprising a liquid permeable absorptive member having an outer facing layer of thermal plastic material and an inner backing layer, said inner backing layer being a material blend of thermal plastic and cellulosic fibers, the outer facing layer of thermal plastic material being ultrasonically welded to the thermal plastic fibers of the blended material inner backing layer to join the layers together while allowing liquid communication throughout the layers, a liquid impervious barrier member underlying the liquid permeable absorptive member to restrict the flow of liquid therethrough, and means attached to the liquid impervious barrier member for lifting and folding the absorptive device without contacting the liquid permeable absorptive member.

2. The absorptive device as defined in claim 1 wherein said means are also made from the same material as said liquid impervious barrier member.

3. The absorptive device as defined in claim 2 wherein the absorptive device is generally square-shaped with rounded corners and said means comprise protective hand pockets which extend diagonally across at least some of said rounded corners in overhanging relationship to said liquid impervious barrier member, said protective hand pockets protecting a user's hand from contact with the liquid permeable absorptive member during lifting and folding of the absorptive device.

4. The absorptive device as defined in claim 3 wherein said protective pockets extend across all of said rounded corner areas.

5. The absorptive device as defined in claim 3 and including a liquid impervious side binding member which overlaps and binds the liquid permeable absorptive member and liquid impervious barrier member to one another along free end surfaces thereof, said protective hand pockets also being attached to the liquid impervious side binding member of said absorptive device along said rounded corner portions.

6. An absorptive device comprising a liquid permeable absorptive member for absorbing liquids in contact therewith, a liquid impervious barrier member underlying the liquid permeable absorptive member to restrict the flow of liquid therethrough, and pocket means attached to and within the confines of the liquid impervious barrier member for lifting and folding the absorptive device without contacting the liquid permeable absorptive member.

7. The absorptive device as defined in claim 6 wherein said pocket means are also made from the same material as said liquid impervious barrier member.

8. The absorptive device as defined in claim 7 wherein the absorptive device is generally square-shaped with rounded corners and said means comprise protective hand pockets which extend diagonally across at least some of said rounded corners in overhanging relationship to said liquid impervious barrier member, said protective hand pockets protecting a user's hand from contact with the liquid permeable absorptive member during lifting and folding of the absorptive device.

9. The absorptive device as defined in claim 8 wherein said protective pockets extend across all of said rounded corner areas.

10. The absorptive device as defined in claim 9 and including a liquid impervious side binding member which overlaps and binds the liquid permeable absorptive member and liquid impervious barrier member to one another along free end surfaces thereof, said protective hand pockets also being attached to the liquid impervious side binding member of said absorptive device along said rounded corner portions.

* * * * *